[19] United States Patent
Ho et al.

[11] Patent Number: 4,863,923
[45] Date of Patent: Sep. 5, 1989

[54] METHOD OF INHIBITING SUPEROXIDE RELEASE

[75] Inventors: Peter P. K. Ho, Carmel; Jill A. Panetta, Zionsville, both of Ind.

[73] Assignee: Eli Lilly and Company, Indianapolis, Ind.

[21] Appl. No.: 214,573

[22] Filed: Jul. 1, 1988

[51] Int. Cl.$^4$ ............... A61K 31/38; C07D 409/06; C07D 409/12; C07D 405/06

[52] U.S. Cl. .................. 514/443; 514/234; 514/326; 514/330; 514/381; 514/382; 514/444; 514/448; 514/465; 514/466; 514/233.5; 514/237.5

[58] Field of Search ............ 514/443, 438, 444, 448, 514/464, 465, 233, 234, 290, 326, 330, 381, 382

[56] References Cited

U.S. PATENT DOCUMENTS

| | | | |
|---|---|---|---|
| 2,857,383 | 10/1958 | Voegtli | 544/376 |
| 3,646,047 | 2/1972 | Wright et al. | 546/202 |
| 4,101,668 | 7/1978 | Samour et al. | 514/443 |
| 4,552,891 | 11/1985 | Ho et al. | 514/443 |
| 4,703,053 | 10/1987 | Connor et al. | 514/382 |

FOREIGN PATENT DOCUMENTS

| | | |
|---|---|---|
| 50957 | 5/1982 | European Pat. Off. |
| 139464 | 5/1985 | European Pat. Off. |
| 146243 | 6/1985 | European Pat. Off. |
| 253650 | 1/1988 | European Pat. Off. |

OTHER PUBLICATIONS

Ho et al., *The Pharmaceologist*, 29 (3), Abstract 359 (1987).
Hornig et al., *JACS*, 74, 5147 (1952).
Campaigne et al., *J. Org. Chem.*, 21, 39 (1956).
Campaigne et al., *J. Org. Chem.*, 26, 359 (1961).
Campaigne et al., *J. Org. Chem.*, 26, 1327 (1961).
Campaigne et al., *J. Med. Chem.*, 10, 945 (1967).
Martynoff, *Compt. Rend.*, 236, 385 (1953).
Goettsch et al., *J. Am. Pharm. Assn.*, 47, 320 (1958).
Walker et al., *J. Org. Chem.*, 28, 3077 (1963).
Shirley et al., *J.A.C.S.*, 75, 3278 (1953).
Gaertner, *J.A.C.S.*, 74, 2185 (1952).
Goettsch, *Dissertation Abstracts*, 17, 2831 (1957).
Ricci, *Annali di Chimica*, 43, 323.
Shirley et al., *J.A.C.S.*, 74, 664 (1952).
Campaigne et al., *J. Het. Chem.*, 12, 889 (1975).
Campaigne et al., *J. Org. Chem.*, 26, 1326 (1961).
Krubsack, *Tet. Letters*, 47, 4823 (1972).
Cooper et al., *J. Chem. Soc.*, 20, 3405 (1971).
Bew et al., *J. Chem. Soc.*, 1314 (1953).
Bonnin et al., *Aust. J. Chem.*, 32, 833 (1979).
Van Zyl et al., *Can. J. Chem.*, 44, 2283 (1966).
Beck, *J. Org. Chem.*, 37, 3224 (1972).
Chakrabarti et al., *Tetrahedron*, 25, 2781 (1969).
Derwent 59399V/33, Abstracting SU 399106.
Israel et al., *Chest*, 94(1) (Supplement), 71S (1988).
Ho et al., Abstracts of the 14th International Congress of Biochemistry, Prague, Czechoslovakia, p. 221, Abstract TU:622 (1988).

*Primary Examiner*—John Kight
*Assistant Examiner*—Nathan M. Nutter
*Attorney, Agent, or Firm*—Robert A. Conrad; Leroy Whitaker

[57] ABSTRACT

A method of inhibiting superoxide release and reducing tissue damage following an inflammatory or ischemic event employing benzothiophenes, benzofurans, and naphthalenes is disclosed.

14 Claims, No Drawings

METHOD OF INHIBITING SUPEROXIDE RELEASE

BACKGROUND OF THE INVENTION

A variety of therapeutic approaches have been attempted in the treatment of post-ischemic tissue injury. Some approaches advocate the scavenging of superoxide free radicals while others suggest the inhibition of enzymes present in the various metabolic pathways, such a the enzyme xanthine oxidase. See, e.g., Simpson, et al., Federation Proceedings, 46 (7), 2413 (1987). Another approach involves the inhibition of superoxide production and release by activated polymorphonuclear leukocytes—see, e.g., Columns 1 and 2 of U.S. Pat. No. 4,668,676. Compounds of this latter class are specially well suited for preventing the formation of toxic oxygen radicals and therefore should be effective agents for minimizing tissue damage resulting from an inflammatory or ischemic event.

SUMMARY OF THE INVENTION

This invention provides a method of inhibiting superoxide release in a mammal which comprises administering an effective amount of a compound of the formula

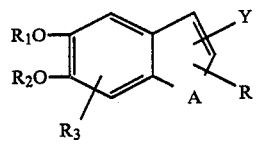 I or a pharmaceutically acceptable salt thereof, wherein
R is hydrogen or methyl;
$R_1$ and $R_2$ are independently $C_1$-$C_5$ alkyl or benzyl;
$R_3$ is hydrogen or chloro;
A is S, O or —CH=CH—; and
Y is —COOH, —CH$_2$OH, —CN, 5-tetrazolyl, or —CONR$_4$R$_5$, where R$_4$ and R$_5$ are each independently hydrogen or $C_1$-$C_3$ alkyl, or when one of R$_4$ and R$_5$ is hydrogen, the other of R$_4$ and R$_5$ may be 5-tetrazolyl, or when taken together with the nitrogen atom to which they are attached, R$_4$ and R$_5$ form a piperidino, morpholino, or N-methyl piperazine ring.

This invention also provides a method of reducing tissue damage in a mammal following an inflammatory or ischemic event by administering to such a mammal an effective amount of a compound of Formula I.

DETAILED DESCRIPTION AND PREFERRED EMBODIMENT

The compounds employed in the present invention are generally taught in U.S. Pat. No. 4,552,891 and EPO Publication No. 253,650, which references are expressly incorporated within this application. In these references, the compounds are taught to be useful for the treatment of asthma by virtue of their ability to inhibit the enzyme phosphodiesterase. The related benzofuran and naphthalene derivatives of this invention are generally known in the art—see, e.g., Horning, et al., J.A.C.S., 74, 5147 (1952) which reference is also expressly incorporated in this application. To the extent compounds described in this application are not specifically taught in any of the above mentioned references, they may be made by analogous chemical means or by other transformations and interconversions as is well known in the art. The pharmaceutical formulations employed in the present invention may also be prepared by methods as described in the above references.

The preferred compounds of the present invention are the benzothiophenes, in particular, benzothiophenes substituted at the 2-position with a carboxylic acid or 5-tetrazolyl moiety. The preferred $R_1$ substituent is ethyl while the preferred $R_2$ substituents include ethyl, propyl and butyl. It is preferred that the R and $R_3$ substituents are each hydrogen.

The terms for the various functional groups employed in this application are illustrated by the compounds described below and are commensurate, to the extent they are consistent with, those terms as used in the above-mentioned references The compounds of the present invention are effective inhibitors of superoxide release. This biological activity was demonstrated by the following test system.

PREPARATION OF HUMAN PMNL

Fresh blood was drawn in sterile syringes with 0.38 percent of sodium citrate/ml of blood. After centrifugation at 200×g for 15 minutes at room temperature, the platelet rich plasma was removed and cells were resuspended in Hanks' balanced salt solution (HBSS) with human serum albumin (HSA) added at 1 mg/ml. Isolation of polymorphonuclear leukocytes (PMNL) is by using 15 ml of Isolymph and layered on top with 15 to 20 ml of defibrinated blood and centrifugated at 200×g for 40 minutes at room temperature. The layers above granulocytes and erythrocytes were removed and 11 ml of 0.2 percent methocel was added to the remaining. The mixture was then placed in a 37° C. bath for 15 minutes. The upper opaque layer of PMNL solution was aspirated and centrifugated at 200×g for 5 minutes. Five ml of 0.2 percent NaCl was added to the red pellet. Immediately after mixing for 30 seconds, 5 ml of 1.5 percent NaCl was added to stop PMNL from lysing. The cell suspension was centrifugated again at 200×g for 5 minutes, and the PMNL were suspended in HBSS with 0.1 HSA. The cell concentration was adjusted to 2×10$^6$ PMNL/ml before assay for superoxide release.

ASSAY FOR SUPEROXIDE RELEASE

Ten microliters of a solution containing various amounts of test compound in HBSS were added to 0.5 ml of the purified PMNL. After 5 minutes of incubation at 37° C., 10$^{-7}$M of PAF (Calbiochem, Calif. U.S.A.), which was prepared by dissolving the powder in HBSS containing 1 mg/ml of HSA, were added to the cell suspensions which were incubated at 37° C. for another 5 minutes. Superoxide generation was then initiated by the addition of 0.5 ml of cytochrome C solution (2 mg/ml) containing 2×10$^{-8}$M of FMLP. Fifteen micrograms of superoxide dismutase (SOD) was used as a standard for the calculation of SOD inhibitable superoxide release. The reactions were all conducted in duplicate. After incubation for 5 minutes at 37° C., the samples were placed in ice water to stop the reaction and centrifuged at 200×g for 15 minutes at 10° C. Supernatants were then transferred to glass tubes for spectrophotometric reading at 550 nm to measure the amount of reduced cytochrome C in μmol/L generated by the superoxide. The results for each compound and concentration are expressed in Table 1 as percent of inhibition as calculated by the following equation:

% Inhibition = 1 −

-continued $$\frac{(\text{Measurement reading} - \text{blank control} - \text{SOD Control}) \times 100}{(\text{PAF and FMLP Control} - \text{blank control} - \text{SOD Control})}$$

The compounds evaluated are labelled as Compounds A-N as follows:

A — 5,6-Diethoxybenzo[b]thiophene-2-carboxylic acid sodium salt
B — 6-Methoxy-5-propoxybenzo[b]thiophene-2-carboxylic acid
C — 4-Chloro-5,6-diethoxybenzo[b]thiophene-2-carboxylic acid
D — 5-(5,6-Diethoxybenzo[b]thien-2-yl)-1H-tetrazole
E — 6-Butoxy-5-ethoxybenzo[b]thiophene-2-carboxylic acid
F — 6-Ethoxy-5-propoxybenzo[b]thiophene-2-carboxylic acid
G — 5-Ethoxy-6-(phenylmethoxy)benzo[b]thiophene-2-carboxylic acid
H — 5,6-Diethoxybenzo[b]thiophene-3-carboxylic acid
I — 5-Ethoxy-6-propoxybenzo[b]thiophene-2-carboxylic acid
J — 6,7-Diethoxy-2-naphthalenecarboxylic acid
K — 5,6-Diethoxybenzo[b]thiophene-2-methanol
L — 6-Ethoxy-5-methoxybenzo[b]thiohpene-2-carboxylic acid
M — 5,6-Diethoxy-3-methylbenzo[b]thiophene-2-carboxylic acid
N — 5,6-Diethoxy-N-1H-tetrazol-5-ylbenzo[b]thiophene-2-carboxamide

TABLE 1

Inhibition of Superoxide Release by Human PMNL Primed by PAF and Stimulated by FMLP

| Compound | Concentrations of Compound (mcg/ml)[1] | | |
|---|---|---|---|
| | 30 | 10 | 3 |
| A | 77[4] | 55[3] | 43[3] |
| B | 77[2] | 45 | 22 |
| C | 59[2] | 13 | 3 |
| D | 88[2] | 47 | 33 |
| E | 99[2] | 69 | 57 |
| F | 92[2] | 58 | 41 |
| G | 74[3] | 48[2] | 43[2] |
| H | 59[3] | 25[2] | 9[2] |
| I | 84 | 68 | 59 |
| J | 69 | 41 | 26 |
| K | 88 | 74 | 73 |
| L | 75 | 59 | 41 |
| M | 87 | 70 | 56 |
| N | 81 | 55 | 30 |

[1] percent inhibition of superoxide release at the given compound concentration
[2] average of two experiments
[3] average of three experiments
[4] average of four experiments The above data indicate the compounds employed in the present invention are useful for inhibiting superoxide release. Accordingly, the further aspect of this invention includes a method of reducing tissue damage in mammals following an inflammatory or ischemic event. Such events include stroke, myocardial infarction, atherosclerosis, general inflammation, arthritis, tissue transplantation, shock, and inflammatory bowel disorders.

To accomplish any of the above-mentioned methods, the compounds may be administered by various routes including the oral, rectal, transdermal, subcutaneous, intravenous, intramuscular, inhalation, or intranasal routes, being usually employed in the form of a pharmaceutical composition. Such compositions are prepared in a manner well known in the pharmaceutical art and comprise at least one compound of Formula I together with a pharmaceutically acceptable carrier, diluent, or excipient therefore. Examples of such formulations are disclosed in U.S. Pat. No. 4,552,891 and EPO No. 253,650.

The compounds of Formula I are effective for the above-mentioned methods over a wide dosage range. Dosages per day will normally fall within the range of 0.5-300 mg/kg. In the treatment of adult humans the range of about 1-50 mg/kg, in single or divided doses, is preferred. However, it will be understood that the amount of compound actually administered will be determined by a physician, in light of the relevant circumstances including the condition to be treated, the choice of compound to be administered, the chosen route of administration, the age, weight and response of the individual patient, and the severity of the patient's symptoms, and therefore the above dosage ranges are not intended to limit the scope of the invention in any way.

Preferably the compositions are formulated in a unit dosage form, each dosage containing from about 5-250 mg of a compound of Formula I. Preferred pharmaceutical forms of the present invention are capsules, tablets, suppositories, injectable solutions, creams and ointments.

We claim:

1. A method of inhibiting superoxide release in a mammal which comprises administering an effective amount of a compound of the formula

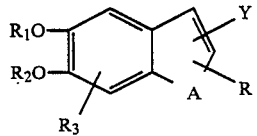

I or a pharmaceutically acceptable salt thereof, wherein
R is hydrogen or methyl;
$R_1$ and $R_2$ are independently $C_1-C_5$ alkyl or benzyl;
$R_3$ is hydrogen or chloro;
A is S, O, or —CH=CH—; and
Y is —COOH, —CH$_2$OH, —CN, 5-tetrazolyl, or —CONR$_4$R$_5$, where $R_4$ and $R_5$ are each independently hydrogen or $C_1-C_3$ alkyl, or when one of $R_4$ and $R_5$ is hydrogen, the other of $R_4$ and $R_5$ may be 5-tetrazolyl, or when taken together with the nitrogen atom to which they are attached, $R_4$ and $R_5$ form a piperidino, morpholino, or N-methyl piperazine ring.

2. The method of claim 1 employing a compound wherein A is S and Y is —COOH or 5-tetrazolyl.

3. The method of claim 2 employing a compound wherein $R_1$ is ethyl.

4. The method of claim 3 wherein $R_2$ is ethyl, propyl, or butyl.

5. The method of claim 4 employing the compound 5,6-diethoxybenzo[b]thiophene-2-carboxylic acid or a pharmaceutically acceptable salt thereof.

6. The method of claim 4 employing the compound 5-ethoxy-6-propoxybenzo[b]thiophene-2-carboxylic acid or a pharmaceutically acceptable salt thereof.

7. The method of claim 4 employing the compound 6-butoxy-5-ethoxybenzo[b]thiophene-2-carboxylic acid or a pharmaceutically acceptable salt thereof.

8. A method of reducing tissue damage in a mammal following an inflammatory or ischemic event which comprises administering to said mammal an effective amount of a compound of the Formula I

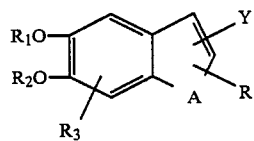

or a pharmaceutically acceptable salt thereof, wherein
R is hydrogen or methyl;
$R_1$ and $R_2$ are independently $C_1$-$C_5$ alkyl or benzyl;
$R_3$ is hydrogen or chloro;
A is S, O, or —CH=CH—; and
Y is —COOH, —CH$_2$OH, —CN, 5-tetrazolyl, or —CONR$_4$R$_5$, where $R_4$ and $R_5$ are each independently hydrogen or $C_1$-$C_3$ alkyl, or when one of $R_4$ and $R_5$ is hydrogen, the other of $R_4$ and $R_5$ may be 5-tetrazolyl, or when taken together with the nitrogen atom to which they are attached, $R_4$ and $R_5$ form a piperidino, morpholino, or N-methyl piperazine ring.

9. The method of claim 8 employing a compound wherein A is S and Y is —COOH or 5-tetrazolyl.

10. The method of claim 9 employing a compound wherein $R_1$ is ethyl.

11. The method of claim 10 wherein $R_2$ is ethyl, propyl, or butyl.

12. The method of claim 11 employing the compound 5,6-diethoxybenzo[b]thiophene-2-carboxylic acid or a pharmaceutically acceptable salt thereof.

13. The method of claim 11 employing the compound 5-ethoxy-6-propoxybenzo[b]thiophene-2-carboxylic acid or a pharmaceutically acceptable salt thereof.

14. The method of claim 11 employing the compound 6-butoxy-5-ethoxybenzo[b]thiophene-2-carboxylic acid or a pharmaceutically acceptable salt thereof.

* * * * *